United States Patent
Bang-Andersen et al.

(10) Patent No.: US 7,105,543 B2
(45) Date of Patent: Sep. 12, 2006

(54) 4-, 5-, 6- AND 7-INDOLE DERIVATIVES USEFUL FOR THE TREATMENT OF CNS DISORDERS

(75) Inventors: Benny Bang-Andersen, Copenhagen S (DK); Jan Kehler, Kgs. Lyngby (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 23 days.

(21) Appl. No.: 11/219,544

(22) Filed: Sep. 1, 2005

(65) Prior Publication Data
US 2006/0004022 A1    Jan. 5, 2006

Related U.S. Application Data

(60) Division of application No. 10/359,052, filed on Feb. 4, 2003, now Pat. No. 6,958,338, which is a continuation of application No. PCT/DK01/00547, filed on Aug. 17, 2001.

(30) Foreign Application Priority Data
Aug. 18, 2000   (DK) ................. 2000 01229

(51) Int. Cl.
A61K 31/4439    (2006.01)
A61K 31/454     (2006.01)
C07D 401/06     (2006.01)

(52) U.S. Cl. ............ 514/323; 514/339; 546/201; 546/277.4; 546/277.7

(58) Field of Classification Search ........ 546/201, 546/277.4, 277.7; 514/323, 339
See application file for complete search history.

(56) References Cited

U.S. PATENT DOCUMENTS

| 4,831,031 | A | 5/1989 | Lowe, III et al. |
| 5,576,336 | A | 11/1996 | Baker et al. |
| 5,670,511 | A | 9/1997 | Marz et al. |
| 5,700,802 | A | 12/1997 | Curtis et al. |
| 6,727,264 | B1 * | 4/2004 | Marzabadi et al. ...... 514/323 |

FOREIGN PATENT DOCUMENTS

| EP | 0164633 | 12/1985 |
| EP | 0281309 | 9/1988 |
| EP | 0722942 | 7/1996 |
| GB | 2310376 | 8/1997 |
| WO | WO-95/29911 | 11/1995 |
| WO | WO-99/37304 | 7/1999 |
| WO | WO-01/29025 | 4/2001 |

OTHER PUBLICATIONS

Akopyan, Zh. G., et al., "Indole derivatives, XXII. Dihydrazides and di(phenylpiperazides) of alpha-alkyl-beta-(2-methyl-5-carboxyindol-3-yl) propionic acids" *Arm. Khim. Zh.* (1968), 21(9): 787-92 (English summary provided), STN International, File CAPLUS, CAPLUS accession No. 1969:413091, Document No. 71:13091.

(Continued)

*Primary Examiner*—Emily Bernhardt
(74) *Attorney, Agent, or Firm*—Darby & Darby

(57) ABSTRACT

The present invention relates to 4-, 5-, 6- or 7-methylene substituted indolyl derivatives of formula I

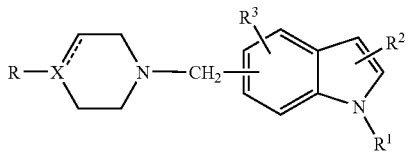

wherein R is aryl or heteroaryl, where said aryl or heteroaryl groups may be substituted one or more times with a substituent seleceted from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl trifluoromethyl, trifluoromethylsulfonyl, $C_{1-6}$-alkylsulfonyl, amino, $C_{1-6}$-alkylamino, di-($C_{1-6}$-alkyl)amino, acyl, aminocarbonyl and a methylene dioxy group;

X is N, C or CH; provided that the dotted line indicates a bond when X is C and no bond when X is N or CH;

$R^1$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl or arylsulfonyl; and $R^2$ and $R^3$ are independently selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl trifluoromethyl, trifluoromethylsulfonyl, $C_{1-6}$-alkylsulfonyl, amino, $C_{1-6}$-alkylamino, di-($C_{1-6}$-alkyl)amino, acyl and aminocarbonyl. The compounds of the invention are selective dopamine $D_4$ ligands.

13 Claims, No Drawings

OTHER PUBLICATIONS

Esayan Z.V., et al., "Indole derivatives. XXVI. Hydrazides and phenylpiperazides of 2-methyl-3-alkylindole-5-carboxylic acids" *Arm. Khim. Zh.* (1969), 22(9): 830-4 (English summary provided), STN International, File CAPLUS, CAPLUS accession No. 1970:21657, Document No. 72:21657.

Esayan et al. Chemical Abstracts, vol. 72, No. 21657w (1970).

LaHoste et al. Medline Abstract for Mol. Psychiatry, vol. 12, p. 121-124 (1996).

TenBrink et al. Journal of Medicinal Chemistry, vol. 39, No. 13, p. 2435-2437 (1996).

Jentsch et al. Psychopharmacology, vol. 142, p. 78-84 (1999).

* cited by examiner

4-, 5-, 6- AND 7-INDOLE DERIVATIVES USEFUL FOR THE TREATMENT OF CNS DISORDERS

CROSS REFERENCE TO RELATED APPLICATIONS

This application is a divisional of application Ser. No. 10/359,052, filed Feb. 4, 2003, now U.S. Pat. No. 6,958,338, which is a continuation of International application no. PCT/DK01/00547, filed Aug. 17, 2001. Each aforementioned prior application is hereby incorporated by reference in its entirety.

FIELD OF THE INVENTION

The present invention relates to a novel class of 4-, 5-, 6- and 7-indole derivatives having affinity for the dopamine $D_4$ receptor. The compounds are useful in the treatment of certain psychiatric and neurologic disorders, in particular psychoses.

BACKGROUND OF THE INVENTION

Dopamine $D_4$ receptors belong to the dopamine $D_2$ subfamily of receptors, which is considered to be responsible for the antipsychotic effects of neuroleptics. The side effects of neuroleptic drugs which primarily exert their effect via antagonism of $D_2$ receptors are known to be due to $D_2$ receptor antagonism in the striatal regions of the brain. However, dopamine $D_4$ receptors are primarily located in areas of the brain other than striatum, suggesting that selective antagonists of the dopamine $D_4$ receptor will be devoid of extrapyramidal side effects. This is illustrated by the antipsychotic clozapine which exerts higher affinity for $D_4$ than $D_2$ receptors and is lacking extrapyramidal side effects (Van Tol et al. *Nature* 1991, 350, 610; Hadley *Medicinal Research Reviews* 1996, 16, 507–526, and Sanner *Exp. Opin. Ther. Patents* 1998, 8, 383–393).

A number of $D_4$ ligands which were postulated to be selective $D_4$ receptor antagonists (L-745,879 and U-101958) have been shown to posses antipsychotic potential (Mansbach et al. *Psychopharmacology* 1998, 135, 194–200). However, recently it has been reported that these compounds are partial $D_4$ receptor agonists in various in vitro efficacy assays (Gazi et al. *Br. J. Pharmacol.* 1998, 124, 889–896 and Gazi et al. *Br. J Pharmacol.* 1999, 128, 613–620). Furthermore, it was shown that clozapine, which is an effective antipsychotic is a silent $D_4$ antagonist (Gazi et al. *Br. J Pharmacol.* 1999, 128, 613–620).

Consequently, $D_4$ ligands, which are partial $D_4$ receptor agonists or antagonists, may have beneficial effects against psychoses.

Dopamine $D_4$ antagonists may also be useful for the treatment of cognitive deficits (Jentsch et al. *Psychopharmacology* 1999, 142, 78–84).

It has also been suggested that selective dopamine $D_4$ antagonists may be useful to reduce dyskinesia occurring as a result of the treatment of Parkinson's disease with L-dopa (Tahar et al. *Eur. J. Pharmacol.* 2000, 399, 183–186).

Furthermore, evidence for a genetic association between the "primarily inattentive" subtype of attention deficit hyperactivity disorder and a tandem duplication polymorphism in the gene encoding the dopamine $D_4$ receptor has been published (McCracken et al. *Mol. Psychiat.* 2000, 5, 531–536). This clearly indicates a link between the dopamine $D_4$ receptor and attention deficit hyperactivity disorder and ligands affecting this receptor may be useful for the treatment of this particular disorder Accordingly, dopamine $D_4$ receptor ligands are potential drugs for the treatment of psychoses, the positive symptoms of schizophrenia, cognitive deficits, attention deficit hyperactivity disorder (ADHD) and dyskinesia resulting from treatment of Parkinson's disease with L-Dopa.

In particular, the compounds of the invention are considered useful in the treatment of positive symptoms of schizophrenia without inducing extrapyramidal side effects.

A number of dopamine $D_4$ ligands which can be described by the general formula

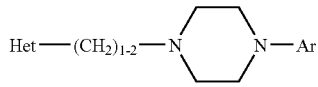

wherein Het is 3-pyrrolo[2,3-b]pyridinyl, 2-benzimidazolyl, 3-indazolyl, 2-indolyl, 3-indolyl, 3-benzofuranyl, imidazo[1,2-a]pyridinyl, 3-furo[2,3-b]pyridinyl and 3-benzofuranyl and Ar is optionally substituted phenyl or heteroaryl, have been described in WO 94/20459, WO 94/20497, WO 94/22839, WO 94/21630, WO 94/24105, WO 99/09025, WO 95/29911, WO 96/25414, U.S. Pat. No. 5,700,802 and *J. Med. Chem.* 1996, 39(19), 1941–2.

EP patent application No. 164 633 relates to compounds of the formula

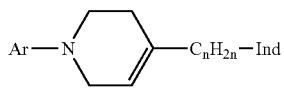

wherein Ar is optionally substituted phenyl or thienyl, n is 2–4 and Ind is optionally substituted 4-indolyl. The compounds are said to inhibit binding of dopamin agonists and -antagonists to striatal receptors and to have sedative, tranquilizing, antidepressive neuroleptic, analgetic and antihypertensive effect. The application does not present any biological test results.

EP patent No. 372 667 relates to compounds having the formula

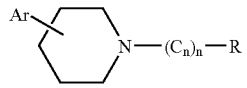

wherein Ar is 2-methoxyphenyl or 1-napthyl, n is 2–4 and R is various heterocyclic rings, e.g. 5-oxindole. The compounds are said to have neuroleptic activity, and data showing the ability of the compounds to bind to dopamine $D_2$ receptors are presented in the application.

EP patent No. 0 281 309 describes certain piperazinyl-heterocyclic compounds of the formula

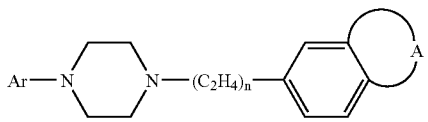

wherein A together with the phenyl to which it is attached form quinolyl, 2-hydroxyquinolyl, benzothiazolyl, 2-aminobenzothiazolyl, benzisothiazolyl, indazolyl, 3-hydroxyindazolyl, indolyl, etc., and Ar is optionally substituted naphthyl, quinolyl, isoquinolyl, indolyl, etc. Notably n is 1 or 2. The compounds are said to be useful for the treatment of psychoses and the mechanism of action is primarily via modulation of the dopamine $D_2$-receptor, the serotonin 5-$HT_{2A}$-receptor and the alpha-adrenergic receptor (J. Med. Chem. 1996, 39, pp.143–148).

According to the present invention, a novel group of compounds which are selective dopamine $D_4$ ligands is provided.

SUMMARY OF THE INVENTION

The object of the present invention is to provide compounds that are partial agonists or antagonists at the dopamine $D_4$ receptor.

Accordingly, the present invention relates to a 4-, 5-, 6- or 7-methylene substituted indolyl derivative of formula I

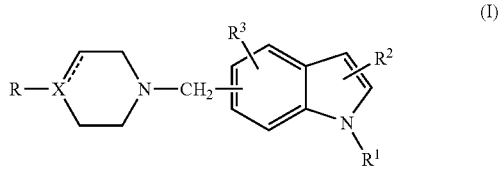

wherein R is aryl or heteroaryl, where said aryl and heteroaryl groups may be substituted one or more times with a substituent selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl trifluoromethyl, trifluoromethylsulfonyl, $C_{1-6}$-alkylsulfonyl, amino, $C_{1-6}$-alkylamino, di-($C_{1-6}$-alkyl) amino, acyl, aminocarbonyl and a methylene dioxy group; X is N, C or CH; provided that the dotted line indicates a bond when X is C and no bond when X is N or CH;

$R^1$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl or arylsulfonyl; and $R^2$ and $R^3$ are independently selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylsulfonyl, hydroxy, hydroxy-$C_{1-6}$-alkyl, trifluoromethyl, trifluoromethylsulfonyl, $C_{1-6}$-alkylsulfonyl, amino, $C_{1-6}$-alkylamino, di-($C_{1-6}$-alkyl)amino, acyl and aminocarbonyl;

Preferred compounds of the invention are compounds selected from:

5-[[4-(4-chlorophenyl)piperazin-1-yl]methyl]-1H-indole
5-[[4-(5-indolyl)piperazin-1-yl]methyl]-1H-indole,
5-[[4-(4-methoxyphenyl)piperazin-1-yl]methyl]-1H-indole
5-[[4-phenylpiperazin-1-yl]methyl]-1H-indole
5-[4-(4-Chlorophenyl)-3,6-dihydro-2H-pyridin-1-ylmethyl]-1H-indole
6-[[4-(4-chlorophenyl)piperazin-1-yl]methyl]-1H-indole,
6-[[4-(4-methoxyphenyl)piperazin-1-yl]methyl]-1H-indole
5-[[4-(4-fluorophenyl)piperazin-1-yl]methyl]-1H-indole
5-[[4-(4-chlorophenyl)piperidin-1-yl]methyl]-1H-indole
5-[[4-(2-chlorophenyl)piperazin-1-yl]methyl]-1H-indole
5-[[4-(3-chlorophenyl)piperazin-1-yl]methyl]-1H-indole
5-[[4-(2,3-dichlorophenyl)piperazin-1-yl]methyl]-1H-indole
5-[[4-(3,4-dichlorophenyl)piperazin-1-yl]methyl]-1H-indole
5-[[4-(4-bromophenyl)piperazin-1-yl]methyl]-1H-indole
5-[[4-(4-iodophenyl)piperazin-1-yl]methyl]-1H-indole
5-[[4-(4-hydroxyphenyl)piperazin-1-yl]methyl]-1H-indole
5-[[4-(2-methoxyphenyl)piperazin-1-yl]methyl]-1H-indole
5-[[4-(3-methoxyphenyl)piperazin-1-yl]methyl]-1H-indole
5-[[4-(3,4-dimethoxyphenyl)piperazin-1-yl]methyl]-1H-indole
5-[[4-(4-methylphenyl)piperazin-1-yl]methyl]-1H-indole
5-[[4-(4-methylphenyl)piperidin-1-yl]methyl]-1H-indole
6-[[4-(4-methylphenyl)piperazin-1-yl]methyl]-1H-indole
6-[[4-(4-methylphenyl)piperidin-1-yl]methyl]-1H-indole
5-[[4-(4-Chlorophenyl)piperazin-1-yl]methyl]-1-methyl-1H-indole
6-[[4-(4-Chlorophenyl)piperazin-1-yl]methyl]-1-methyl-1H-indole
5-[[(4-Benzo[1,3]dioxol-5-yl-)piperazin-1-yl]methyl]-1H-indole or a pharmaceutically acceptable salt thereof.

In one embodiment, the present invention relates to such compounds wherein the indole is attached to the group

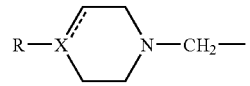

via the 5-position or the 6-position of the indole, in particular the 5-position.

In another embodiment, the present invention relates to such compounds wherein R is optionally substituted phenyl.

In another particular embodiment, the invention relates to a compound as above wherein R is a group of formula

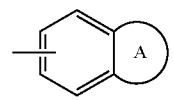

wherein A is an optionally substituted, saturated or unsaturated heterocyclic ring which may contain one or two heteroatoms selected from N, O and S. The substituents may be one or more substituents selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl, trifluoromethyl, trifluoromethylsulfonyl, $C_{1-6}$-alkylsulfonyl, amino, $C_{1-6}$-alkylamino, di-($C_{1-6}$-alkyl)amino, acyl and aminocarbonyl In a particular embodiment of the invention, R is optionally substituted indolyl or phenyl substituted by a methylene dioxy group.

In a further particular another embodiment, the present invention relates to such compounds wherein R is optionally substituted 5- or 6-indolyl.

The invention includes in particular such compounds wherein X is N and the dotted line is no bond.

The compounds according to the invention also include compounds wherein X is C and the dotted line is a bond.

The invention also includes compounds wherein X is CH and the dotted line is no bond.

In a further embodiment, the invention relates to compounds wherein R is phenyl which is optionally substituted one or more times with substituents selected from halogen, trifluoromethyl, nitro, cyano, $C_{1-6}$-alkyl, $C_{1-6}$-alkoxy, hydroxy and a methylene dioxy group.

In another embodiment, the invention relates to compounds wherein R is indolyl which is optionally substituted one or more times with substituents selected from halogen, trifluoromethyl, nitro, cyano, $C_{1-6}$-alkyl, $C_{1-6}$-alkoxy and hydroxy.

The compounds of the invention are partial agonists or antagonist at the dopamine $D_4$ receptors.

Accordingly, the compounds of the invention are considered useful in the treatment of psychoses, positive symptoms of schizophrenia, cognitive deficits, ADHD and dyskinesia resulting from treatment of Parkinson's disease with L-Dopa.

In particular, the compounds of the invention are considered useful in the treatment of positive symptoms of schizophrenia without inducing extrapyramidal side effects.

Thus, in another aspect, the present invention provides a pharmaceutical composition comprising at least one compound of formula I as defined above or a pharmaceutically acceptable acid addition salt thereof in a therapeutically effective amount and in combination with one or more pharmaceutically acceptable carriers or diluents.

In a further aspect, the present invention provides the use of a compound of formula I as defined above or an acid addition salt thereof for the manufacture of a pharmaceutical preparation for the treatment of the above mentioned disorders.

DETAILED DESCRIPTION OF THE INVENTION

The compounds of the general formula I may exist as optical isomers thereof and such optical isomers are also embraced by the invention.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$-alkenyl and $C_{2-6}$-alkynyl, respectively, designate such groups having from two to six carbon atoms, including one double bond and one triple bond, respectively, such as ethenyl, propenyl, butenyl, ethynyl, propynyl and butynyl.

The term $C_{3-8}$-cycloalkyl designates a monocyclic or bicyclic carbocycle having three to eight C-atoms, such as cyclopropyl, cyclopentyl, cyclohexyl, etc.

Halogen means fluoro, chloro, bromo or iodo.

As used herein, the term acyl refers to a formyl, $C_{1-6}$-alkylcarbonyl, arylcarbonyl, aryl-$C_{1-6}$-alkylcarbonyl, $C_{3-8}$-cycloalkylcarbonyl or a $C_{3-8}$-cycloalkyl-$C_{1-6}$-alkyl-carbonyl group and the term thioacyl is the corresponding acyl group, in which the carbonyl group is replaced with a thiocarbonyl group.

The terms $C_{1-6}$-alkoxy, $C_{3-8}$-cycloalkyl-$C_{1-6}$-alkyl, $C_{1-6}$-alkylsulfonyl, $C_{1-6}$-alkylamino, $C_{1-6}$-alkylcarbonyl, and the like, designate such groups in which the alkyl group is $C_{1-6}$ alkyl and $C_{1-6}$ alkyl and the $C_{3-8}$-cycloalkyl group are as defined above.

The term aryl refers to a carbocyclic aromatic group, such as phenyl or naphthyl, in particular phenyl.

The term heteroaryl refers to 5-membered monocyclic rings such as 1H-tetrazolyl, 3H-1,2,3-oxathiazolyl, 3H-1,2,4-oxathiazolyl, 3H-1,2,5-oxathiazolyl, 1,3,2-oxathiazolyl, 1,3,4-oxathiazolyl, 1,4,2-oxathiazolyl, 3H-1,2,4-dioxazolyl, 1,3,2-dioxazolyl, 1,4,2-dioxazolyl, 3H-1,2,3-dithiazolyl, 3H-1,2,4-dithiazolyl, 1,3,2-dithiazolyl, 1,4,2-dithiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-1,2,3-triazolyl, 1H-1,2,4-triazolyl, isoxazolyl, oxazolyl, isothiazolyl, thiazolyl, 1H-imidazolyl, 1H-pyrazolyl, 1H-pyrrolyl, furanyl, thienyl, 1H-pentazole, 6-membered monocyclic rings such as 1,2,3-oxathiazinyl, 1,2,4-oxathiazinyl, 1,2,5-oxathiazinyl, 4H-1,3,5-oxathiazinyl, 1,4,2-oxathiazinyl, 1,4,3-oxathiazinyl, 1,2,3-dioxazinyl, 1,2,4-dioxazinyl, 4H-1,3,2-dioxazinyl, 4H-1,3,5-dioxazinyl, 1,4,2-dioxazinyl, 2H-1,5,2-dioxazinyl, 1,2,3-dithiazinyl, 1,2,4-dithiazinyl, 4H-1,3,2-dithiazinyl, 4H-1,3,5-dithiazinyl 1,4,2-dithiazinyl, 2H-1,5,2-dithiazinyl, 2H-1,2,3-oxadiazinyl, 2H-1,2,4-oxadiazinyl, 2H-1,2,5-oxadiazinyl, 2H-1,2,6-oxadiazinyl, 2H-1,3,4-oxadiazinyl, 2H-1,3,5-oxadiazinyl, 2H-1,2,3-thiadiazinyl, 2H-1,2,4-thiadiazinyl, 2H-1,2,5-thiadiazinyl, 2H-1,2,6-thiadiazinyl, 2H-1,3,4-thiadiazinyl, 2H-1,3,5-thiadiazinyl, 1,2,3-triazinyl, 1,2,4-triazinyl, 1,3,5-triazinyl, 2H-1,2-oxazinyl, 2H-1,3-oxazinyl, 2H-1,4-oxazinyl, 2H-1,2-thiazinyl, 2H-1,3-thiazinyl, 2H-1,4-thiazinyl, pyrazinyl, pyridazinyl, pyrimidyl, pyridyl, 2H-pyranyl, 2H-thiinyl and to bicyclic rings such as 3H-1,2,3-benzoxathiazolyl, 1,3,2-benzodioxazolyl, 3H-1,2,3-benzodithiazolyl, 1,3,2-benzodithiazolyl, benzfurazanyl, 1,2,3-benzoxadiazolyl, 1,2,3-benzothiadiazolyl, 2,1,3-benzothiadiazolyl, 1H-benzotriazolyl, 1,2-benzisoxazolyl, 2,1-benzisoxazolyl, benzoxazolyl, 1,2-benzisothiazolyl, 2,1-benzisothiazolyl, benzothiazolyl, 1H-benzimidazolyl, 1H-indazolyl, 3H-1,2-benzoxathiolyl, 1,3-benzoxathiolyl, 3H-2,1-benzoxathiolyl, 3H-1,2-benzodioxolyl, 1,3-benzodioxolyl 3H-1,2-benzodithiolyl, 1,3-benzodithiolyl, 1H-indolyl, 2H-isoindolyl, benzofuranyl, isobenzofuranyl, 1-benzothienyl, 2-benzothienyl, 1H-2,1-benzoxazinyl, 1H-2,3-benzoxazinyl, 2H-1,2-benzoxazinyl, 2H-1,3-benzoxazinyl, 2H-1,4-benzoxazinyl, 2H-3,1-benzoxazinyl, 1H-2,1-benzothiazinyl, 1H-2,3-benzothiazinyl, 2H-1,2-benzothiazinyl, 2H-1,3-benzothiazinyl, 2H-1,4-benzothiazinyl, 2H-3,1-benzothiazinyl, cinnolinyl, phtalazinyl, quinazolinyl, quinoxalinyl, isoquinolyl, quinolyl, 1H-2-benzopyranyl, 2H-1-benzopyranyl, 1H-2-benzothiopyranyl or 2H-1-benzothiopyranyl.

In a particular embodiment, the invention relates to a compound as above wherein R is a group of formula

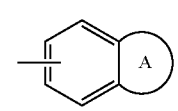

wherein A is an optionally substituted, saturated or unsaturated heterocyclic ring which may contain one or two heteroatoms selected from N, O and S. The formula covers for example such bicyclic rings which are mentioned in the list above. The substituents on A may be one or more substituents selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl trifluoromethyl, trifluoromethylsulfonyl, $C_{1-6}$-alkylsulfonyl, amino, $C_{1-6}$-alkylamino, di-($C_{1-6}$-alkyl)amino, acyl and aminocarbonyl.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The pharmaceutical compositions of this invention, or those which are manufactured in accordance with this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The compounds of the invention may be prepared as follows:

a) Reducing the amide group of a compound of formula II

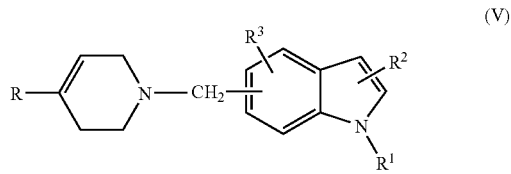

(II)

wherein R, $R^1$, $R^2$, $R^3$, X and the dotted line are as previously defined.

b) Reductive alkylation of an amine of the formula III with an aldehyde of formula IV

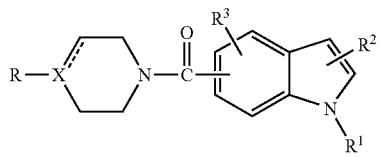

(III)

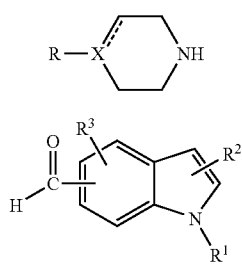

(IV)

wherein R, $R^1$, $R^2$, $R^3$, X and the dotted line are as previously defined.

c) Reducing the double bond in the tetrahydropyridinyl ring in derivatives of formula V:

(V)

wherein R, $R^1$, $R^2$, $R^3$, X and the dotted line are as previously defined.

The reduction according to method a) is preferably carried out in an inert organic solvent such as diethyl ether or tetrahydrofuran in the presence of alane or lithium aluminium hydride from 0° C. to reflux temperature. Starting compounds of formula (II) are generally prepared by coupling of an amine of formula (III) with an appropriately substituted indolyl carboxylic acid by standard methods via the carboxylic acid chloride, activated esters or by the use of carboxylic acids in combination with a coupling reagent such as e.g. dicyclohexyl carbodiimide. Amines of formula (III) are either commercially available or can be prepared by standard literature methods (see e.g. *J. Med. Chem.* 1991, 34, 2014–2023; *J. Med. Chem.* 1998, 41, 658–667). 3-(piperidin-4-yl)-1H-indoles and (3,6-dihydro-2H-pyridin-4-yl)-1H-indoles have been described in the literature (see EP-A1-465398).

The reduction according to method b) is carried out by a standard one-pot procedure, e.g. using a reductive amination of amines of formula (III) and aldehydes of formula (IV). Starting compounds of formula (IV) and appropriately substituted indolyl carboxylic acids are either commercially available or can be synthesised by methods described in the literature or in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions.

The reduction of the double bond according to method c) is generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran (THF), dioxane or diethyl ether.

Experimental Section

Melting points were determined on a Büchi SMP-20 apparatus and are uncorrected. Analytical LC-MS data were obtained on a PE Sciex API 150EX instrument equipped with IonSpray source and Shimadzu LC-8A/SLC-10A LC system. The LC conditions (C18 column 4.6×30 mm with a particle size of 3.5 μm) were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times, $R_t$, are expressed in minutes.

Mass spectra were obtained by an alternating scan method to give molecular weight information. The molecular ion, MH+, was obtained at low orifice voltage (5–20V) and fragmentation at high orifice voltage (100–200V).

Preparative LC-MS-separation was performed on the same instrument. The LC conditions (C18 column 20×50 mm with a particle size of 5 μm) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. For column chromatography silica gel of type Kieselgel 60, 230–400 mesh ASTM was used. For ion-exchange chromatography (SCX, 1 g, Varian Mega Bond Elut®, Chrompack cat. No. 220776) was used. Prior use of the SCX-columns was pre-conditioned with 10% solution of acetic acid in methanol (3 mL).

EXAMPLES 1a, 5-[[4-(4-chlorophenyl)piperazin-1-yl]methyl]-1H-indole

Indole-5-carboxylic acid (1.62 g) was dissolved in dry THF (20 mL). Carbonyl diimidazole (1.62 g) was added, and the mixture was stirred at room temperature for 60 min. 4-(4-chlorophenyl)piperazine (1.9 g) dissolved in dry THF (20 mL) was added in one portion and the mixture was stirred at room temperature for 5 h. The solvent was removed in vacuo, and the remaining solid was dissolved in EtOAc (400 mL), washed with 10% aqueous sodium carbonate (100 mL), 1 M acetic acid (100 ml), brine (100 mL), dried (MgSO$_4$) and evaporated in vacuo to give a white solid (2.3 g). The solid was dissolved in dry THF (40 mL) and subsequently added dropwise to a cooled solution of alane in THF (prepared by the careful addition of 0.6 g conc. sulfuric acid to a suspension of 0.47 g lithium aluminium hydride in 20 mL dry THF). The mixture was stirred at 15° C. for 2 h, quenched by the addition of water (1 mL), conc. NaOH (½ mL) and water (2 mL). The white precipitate was removed by filtration and the THF evaporated in vacuo to give the product as a white solid. Recrystallisation from MeCN gave 1.8 g 5-[[4-(4-chlorophenyl)piperazin-1-yl]methyl]indole as white crystals. Mp 175–176° C.; Analysis calcd. (C$_{19}$H$_{20}$ClN$_3$): C:70.04, H: 6.19, N: 12.90: found. C: 69.94, H: 6.25, N: 12.90. $^1$H NMR (DMSO-d$_6$): 3.10 (m, 4H); 3.40 (m, 4H); 3.50 (s, 2H); 6.40 (s, 1H); 6.90 (d, 2H); 7.10 (d, 1H); 7.21 (d, 2H); 7.30 (m, 2H); 7.45 (s, 1H).

The following compound was prepared in a similar manner:

1b, 5-[[4-(5-indolyl)piperazin-1-yl]methyl]-1H-indole, $^1$H NMR (DMSO-d$_6$): 2.55 (m, 4H); 3.00 (m, 4H); 3.50 (s, 2H); 6.25 (s, 1H), 6.45 (s, 1H); 6.85 (m, 1H); 6.95 (m, 1H); 7.05 (m, 1H); 7.20 (m, 3H); 7.30 (m, 2H); 7.45 (s, 1H); 10.80 (s, 1H); 11.00 (s, 1H).

1c, 5-[[4-(4-methoxyphenyl)piperazin-1-yl]methyl]-1H-indole $^1$H NMR (DMSO-d$_6$): 2.60 (m, 4H); 3.10 (m, 4H); 3.60 (s, 2H); 3.70 (s, 3H); 6.40 (s, 1H); 6.80 (d, 2H); 6.90 (m, 2H), 6.95 (d, 1H); 7.30 (m, 2H); 7.45 (m, 1H), 11.00 (s, 1H).

1d, 5-[[4-phenylpiperazin-1-yl]methyl]-1H-indole $^1$H NMR (DMSO-d$_6$): 2.60 (m, 4H); 3.10 (m, 4H); 3.60 (s, 2H); 6.35 (s, 1H); 6.75 (m, 1H); 6.90 (m, 2H); 7.05 (m, 1H); 7.15 (m, 2H); 7.35 (m, 2H); 7.45 (s, 1H); 11.00 (s, 1H).

1e, 5-[4-(4-Chlorophenyl)-3,6-dihydro-2H-pyridin-1-ylmethyl]-1H-indole $^1$H NMR (DMSO-d$_6$): 2.45 (m, 2H); 2.65 (m, 2H), 3.05 (m, 2H); 3.60 (s, 2H); 6.20 (m, 1H), 6.40 (s, 1H); 7.10 (m, 1H); 7.30-7.40 (m, 4H); 7.40-7.50 (m, 3H); 11.00 (s, 1H).

1f, 6-[[4-(4-chlorophenyl)piperazin-1-yl]methyl]-1H-indole $^1$H NMR (DMSO-d$_6$): 2.55 (m, 4H); 3.10 (m, 4H); 3.60 (s, 2H); 6.40 (s, 1H); 6.90 (d, 2H); 7.10 (d, 1H); 7.20 (d, 2H); 7.30 (m, 2H); 7.45 (s, 1H), 11.00 (s, 1H).

1g, 6-[[4-(4-methoxyphenyl)piperazin-1-yl]methyl]-1H-indole $^1$H NMR (DMSO-d$_6$): 2.55 (m, 4H); 3.00 (m, 4H); 3.60 (s, 2H); 3.70 (s, 3H); 6.40 (s, 1H); 6.80 (d, 2H); 6.90 (m, 2H), 6.95 (d, 1H); 7.30 (m, 2H); 7.45 (m, 1H), 11.00 (s, 1H 1h, 5-[4-(4-Fluorophenyl)-piperidin-1-ylmethyl]-1H-indole $^1$H NMR (DMSO-d$_6$): 1.60 (m, 2H); 1.70 (m, 2H), 2.00 (m, 2H); 2.95 (m, 2H); 3.50 (s, 2H); 6.40 (s, 1H); 7.10 (m, 3H); 7.30–7.40 (m, 4H); 7.45 (m, 1H); 11.00 (s, 1H).

1i, 6-[4-(4-Chlorophenyl)-piperazin-1-ylmethyl]-1-methyl-1H-indole, $^1$H NMR (DMSO-d$_6$): 2.55 (m, 4H); 3.10 (m, 4H); 3.60 (s, 2H); 3.70 (s, 3H), 6.40 (s, 1H); 6.90 (d, 2H); 7.10 (d, 1H); 7.20 (d, 2H); 7.30 (m, 2H); 7.45 (s, 1H), 11.00 (s, 1H).

1j, 6-[4-(4-Fluorophenyl)-piperidin-1-ylmethyl]-1H-indole $^1$H NMR (DMSO-d$_6$): 1.60 (m, 2H); 1.70 (m, 2H), 2.00 (m, 2H); 2.95 (m, 2H); 3.50 (s, 2H); 6.40 (s, 1H); 6.95 (d, 1H), 7.10 (m, 2H); 7.30–7.40 (m, 4H); 7.45 (m, 1H); 11.00 (s, 1H).

1k, 5-[4-(4-Chlorophenyl)-piperazin-1-ylmethyl]-1-methyl-1H-indole, $^1$H NMR (DMSO-d$_6$): 2.55 (m, 4H); 3.10 (m, 4H); 3.60 (s, 2H); 3.70 (s, 3H), 6.40 (s, 1H); 6.90 (d, 2H); 7.10 (d, 1H); 7.20 (d, 2H); 7.30 (m, 1H); 7.40 (m, 1H); 7.50 (s, 1H), 11.00 (s, 1H).

1l, 5-[4-(4-Chlorophenyl)-piperidin-1-ylmethyl]-1H-indole, $^1$H NMR (DMSO-$d_6$): 2.55 (m, 4H); 3.10 (m, 4H); 3.60 (s, 2H); 6.40 (s, 1H); 6.90 (d, 2H); 7.10 (d, 1H); 7.20 (d, 2H); 7.30 (m, 1H); 7.40 (m, 1H), 7.50 (s, 1H), 11.00 (s, 1H).

The following compounds may also be prepared according to the invention:
5-[[4-(4-fluorophenyl)piperazin-1-yl]methyl]-1H-indole
5-[[4-(4-chlorophenyl)piperidin-1-yl]methyl]-1H-indole
5-[[4-(2-chlorophenyl)piperazin-1-yl]methyl]-1H-indole
5-[[4-(3-chlorophenyl)piperazin-1-yl]methyl]-1H-indole
5-[[4-(2,3-dichlorophenyl)piperazin-1-yl]methyl]-1H-indole
5-[[4-(3,4-dichlorophenyl)piperazin-1-yl]methyl]-1H-indole
5-[[4-(4-bromophenyl)piperazin-1-yl]methyl]-1H-indole
5-[[4-(4-iodophenyl)piperazin-1-yl]methyl]-1H-indole
5-[[4-(4-hydroxyphenyl)piperazin-1-yl]methyl]-1H-indole
5-[[4-(2-methoxyphenyl)piperazin-1-yl]methyl]-1H-indole
5-[[4-(3-methoxyphenyl)piperazin-1-yl]methyl]-1H-indole
5-[[4-(3,4-dimethoxyphenyl)piperazin-1-yl]methyl]-1H-indole
5-[[4-(4-methylphenyl)piperazin-1-yl]methyl]-1H-indole
5-[[4-(4-methylphenyl)piperidin-1-yl]methyl]-1H-indole
6-[[4-(4-methylphenyl)piperazin-1-yl]methyl]-1H-indole
6-[[4-(4-methylphenyl)piperidin-1-yl]methyl]-1H-indole
5-[[4-(4-Chlorophenyl)piperazin-1-yl]methyl]-1-methyl-1H-indole
6-[[4-(4-Chlorophenyl)piperazin-1-yl]methyl]-1-methyl-1H-indole
5-[[(4-Benzo[1,3]dioxol-5-yl-)piperazin-1-yl]methyl]-1H-indole Pharmacological Testing The compounds of the invention were tested in well-recognised and reliable tests. The tests were as follows:

Inhibition of Binding of [$^3$H]YM-09151-2 to $D_{4.2}$ Receptors

By this method, the inhibition by drugs of the binding of [$^3$H]YM-09151-2 (0.06 nM) to membranes of human cloned dopamine $D_{4.2}$ receptors expressed in CHO-cells is determined in vitro. The method is modified from NEN Life Science Products, Inc., technical data certificate PC2533-10/96.

Inhibition of the Binding of [$^3$H]Spiperone to $D_2$ Receptors

The compounds were tested with respect to affinity for the dopamine $D_2$ receptor by determining their ability to inhibit the binding of [$^3$H]Spiperone to $D_2$ receptors by the method of Hyttel et al. *J. Neurochem.* 1985, 44, 1615.

In table 1 below, the test results are shown:

| Receptor | $D_2$-Receptor IC50 (nM) | $D_4$-receptor IC50 (nM) |
| --- | --- | --- |
| 1a | 1700 | 7.5 |
| 1b | 1000 | <50/89 |
| 1c | >10000 | 25 |
| 1d | 940 | 31 |
| 1e | 190 | 1.4 |
| 1f | >10000 | |
| 1g | >10000 | 9.1 |

The tested compounds were found potently to inhibit the binding of tritiated YM-09151-2 to dopamine $D_4$ receptors.

The compounds were also tested in a functional assay described by Gazi et al. in *Br. J. Pharmacol.* 1999, 128, 613–629. In this test, the compounds were shown to be partial agonists or antagonists at the dopamine $D_4$ receptors.

The compounds were found to have no substantial or only weak affinity for the dopamine $D_2$ receptor.

Thus, the compounds of the invention are considered useful in the treatment of psychoses, positive and negative symptoms of schizophrenia, cognitive disorders, ADHD and dyskinesia resulting from treatment of Parkinson's disease with L-Dopa.

In particular, the compounds of the invention are considered useful in the treatment of positive and negative symptoms of schizophrenia without inducing extrapyramidal side effects.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| | |
| --- | --- |
| Compound 1a or 1b | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
| --- | --- |
| Compound 1a or 1b | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
| --- | --- |
| Compound 1a or 1b | 25 mg |
| Sorbitol | 500 mg |
| Hydroxypropylcellulose | 15 mg |

-continued

|  |  |
|---|---|
| Glycerol | 50 mg |
| Methyl-paraben | 1 mg |
| Propyl-paraben | 0.1 mg |
| Ethanol | 0.005 ml |
| Flavour | 0.05 mg |
| Saccharin sodium | 0.5 mg |
| Water | ad 1 ml |

4) Solution for injection containing per millilitre:

|  |  |
|---|---|
| Compound 1a or 1b | 0.5 mg |
| Sorbitol | 5.1 mg |
| Acetic Acid | 0.05 mg |
| Saccharin sodium | 0.5 mg |
| Water | ad 1 ml |

The invention claimed is:

1. A 4-, 5-, 6- or 7-methylene substituted indolyl derivative of formula I

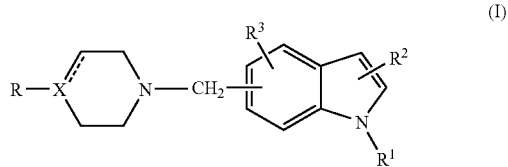

wherein R is aryl or indolyl, where said aryl or indolyl group may be substituted one or more times with a substituent selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$alkoxy, $C_{1-6}$-alkylthio, hydroxy, hydroxy-$C_{1-6}$-alkyl, trifluoromethyl, trifluoromethylsulfonyl, $C_{1-6}$-alkylsulfonyl, amino, $C_{1-6}$-alkylamino, di-($C_{1-6}$-alkyl) amino, acyl, aminocarbonyl and a methylene dioxy group;

X is C or CH; provided that the dotted line indicates a bond when X is C and no bond when X is CH;

$R^1$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl or arylsulfonyl; and $R^2$ and $R^3$ are independently selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkoxy, $C_{1-6}$-alkylthio, hydroxy, hydroxy-$C_{1-6}$-alkyl, trifluoromethyl, trifluoromethylsulfonyl, $C_{1-6}$-alkylsulfonyl, amino, $C_{1-6}$-alkylamino, di-($C_{1-6}$-alkyl) amino, acyl and aminocarbonyl;

or a pharmaceutically acceptable salt thereof.

2. The compound according to claim 1, wherein Formula I is represented by the formula

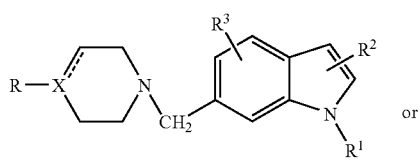 or

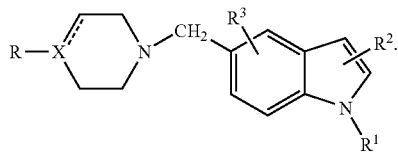

3. The compound according to claim 1 or 2, wherein R is optionally substituted phenyl.

4. The compound according to claim 1 or 2, wherein R is optionally substituted indolyl or phenyl substituted by a methylene dioxy group.

5. The compound according to claim 1 or 2, wherein X is C.

6. The compound according to claim 1 or 2, wherein X is CH.

7. The compound according to claim 3, wherein the phenyl group R is optionally substituted one or more times with substituents selected from halogen, trifluoromethyl, nitro, cyano, $C_{1-6}$-alkyl, $C_{1-6}$-alkoxy, hydroxy and a methylene dioxy group.

8. The compound according to claim 1 or 2, wherein the group R is optionally substituted one or more times with substituents selected from halogen, trifluoromethyl, nitro, cyano, $C_{1-6}$-alkyl, $C_{1-6}$-alkoxy and hydroxy.

9. The compound according to claim 1, which is

5-[4-(4-chlorophenyl)-3,6-dihydro-2H-pyridin-1-ylmethyl]-1H-indole;

5-[[4-(4-chlorophenyl)piperidin-1-yl]methyl]-1H-indole;

5-[[4-(4-methylphenyl)piperidin-1-yl]methyl]-1H-indole;

6-[[4-(4-methylphenyl)piperidin-1-yl]methyl]-1H-indole;

5-[4-(4-fluorophenyl)-piperidin-1-ylmethyl]-1H-indole;

6-[4-(4-fluorophenyl)-piperidin-1-ylmethyl]-1H-indole;

or a pharmaceutically acceptable salt thereof.

10. The compound of claim 2, wherein Formula I is represented by the formula

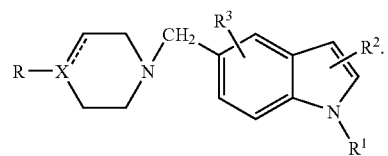

11. A pharmaceutical composition comprising a compound of claim 1 in a therapeutically effective amount, together with one or more pharmaceutically acceptable carriers or diluents.

12. A method of treating psychoses comprising administering a therapeutically acceptable amount of a compound according to claim 1.

13. The method of claim 12 wherein the method of treating psychoses is a method of treating the positive symptoms of schizophrenia.

* * * * *